(12) United States Patent
Henryon et al.

(10) Patent No.: US 8,822,706 B2
(45) Date of Patent: Sep. 2, 2014

(54) METHOD FOR PREPARING 2-HYDROXYBUTYROLACTONE

(75) Inventors: Vivien Henryon, Lyons (FR); Jerome Monbrun, Chuzelles (FR)

(73) Assignee: Adisseo France S.A.S., Antony (FR)

( * ) Notice: Subject to any disclaimer, the term of this patent is extended or adjusted under 35 U.S.C. 154(b) by 0 days.

(21) Appl. No.: 13/879,442

(22) PCT Filed: Oct. 17, 2011

(86) PCT No.: PCT/FR2011/052417
§ 371 (c)(1),
(2), (4) Date: Apr. 15, 2013

(87) PCT Pub. No.: WO2012/049435
PCT Pub. Date: Apr. 19, 2012

(65) Prior Publication Data
US 2013/0204016 A1    Aug. 8, 2013

(30) Foreign Application Priority Data

Oct. 15, 2010 (FR) ...................................... 10 58440

(51) Int. Cl.
C07D 307/33 (2006.01)
C07C 29/09 (2006.01)

(52) U.S. Cl.
USPC ........................................................ 549/313

(58) Field of Classification Search
CPC .................................................... C07D 307/33
USPC ........................................................ 549/313
See application file for complete search history.

(56) References Cited

FOREIGN PATENT DOCUMENTS

FR    2150605 A1    4/1973
WO   2008022953 A1  2/2008

OTHER PUBLICATIONS

Christian Daremon ET Rene Rambaud: 1-14; "Obtention et etude de quelques gamma-butanol ides alpha-substitues (ler memoire)", Bulletin De La Societe Chimique De France, Societe Francaise De Chimie. Paris,France, No. I, 1971, pp. 294-301.

*Primary Examiner* — Nizal Chandrakumar
(74) *Attorney, Agent, or Firm* — Porzio, Bromberg & Newman, P.C.

(57) ABSTRACT

The invention relates to a method for preparing 2-hydroxybutyrolactone (2HBL) from a compound or its salt or its oligomers, said compound fitting formula (I)

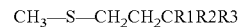

Wherein
R1 represents H
R2 represents a group selected from OH; OR4 and OCOR4 wherein R4 represents a group selected from linear, cyclic, alicyclic or branches alkyl groups having from 1 to 10 carbon atoms, and aryl groups having from 6 to 10 carbon atoms, optionally substituted with substituent(s) selected from linear or branched alkyl groups having from 1 to 10 carbon atoms, halogens and hydroxyl, amino, nitro and alkoxy groups having from 1 to 10 carbon atoms; and OSiRR'R" wherein R, R' and R" are selected independently of each other from linear, cyclic, alicyclic or branched alkyl groups having from 1 to 10 carbon atoms, aryl groups having from 6 to 10 carbon atoms, optionally substituted with substituent(s) selected from linear or branched alkyl groups having from 1 to 10 carbon atoms, or R1 and R2 represent together $=O$,
R3 represents COOH or a COOR5 group wherein R5 represents a group selected from linear, cyclic, alicyclic or branched alkyl groups having from 1 to 10 carbon atoms, benzyl groups and benzyl groups substituted with one or two substituents selected from linear or branched alkyl groups having from 1 to 10 carbon atoms, halogens and hydroxyl, amino, nitro and alkoxy groups having from 1 to 10 carbon atoms, or R3 represents a cyano group,
method according to which
a sulfonium of said compound is obtained, said sulfonium fitting the formula (II)

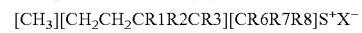

wherein R1, R2 and R3 have the above definition, and R6 and R7 are selected independently of each other from H, linear, cyclic, alicyclic or branched alkyl groups having from 1 to 10 carbon atoms, and aryl groups having from 6 to 10 carbon atoms, optionally substituted with substituent(s) selected from linear or branched alkyl groups having from 1 to 10 carbon atoms, halides and hydroxyl, amino, nitro and alkoxy groups having from 1 to 10 carbon atoms; R8 is selected from H, linear, cyclic, alicyclic or branched alkyl groups having from 1 to 10 carbon atoms, aryl groups having from 6 to 10 carbon atoms, optionally substituted with substituent(s) selected from linear or branched alkyl groups having from 1 to 10 carbon atoms, and attractor groups notably those comprising a function selected from acid, ester, cyano functions and X represents a counter-ion, and the thereby obtained sulfonium is hydrolyzed and 2,4-dihydroxybutyric acid or its salt is cyclized into 2-hydroxybutyrolactone.

13 Claims, No Drawings

METHOD FOR PREPARING 2-HYDROXYBUTYROLACTONE

CROSS REFERENCE TO RELATED APPLICATION

This is a National Stage of International Application No. PCT/FR2011/052417, filed 17 Oct. 2011, which claims the benefit of application Ser. No. 10/58440, filed in France on 15 Oct. 2010, the disclosures of which Applications are incorporated by reference herein.

The present invention relates to a method for preparing 2-hydroxybutyrolactone (2HBL) from 2-hydroxy-4-methylthiobutyric acid (equally abbreviated as HMTBA, HMBA, AT88 or Rhodimet AT88), from its oxo analog, 2-oxo-4-methylthiobutyric acid (abbreviated as KMB), 2-hydroxy-4-methylthiobutyronitrile, as well as from their derivatives.

2HBL is an important synthesis intermediate. It may be prepared industrially in a known way from malic acid in three steps (DE19735575A1, AU2004200948A), or from γ-butyrolactone in two steps (WO2008/022953A1, Bull. Soc. Chim. Fr. 1971, 1, 294-301).

The problem posed by these two routes lies in the difficulty in isolating 2HBL on the one hand and in a very significant production of salts on the other hand which have then to be removed. The first synthesis route further has the drawbacks of engaging expensive reagents, i.e. $BH_3$ and TFAA; the use of borane more particularly requires specific safety conditions. The second access route uses toxic reagents, i.e. $Br_2$ and $PBr_3$ and the performances described according to this strategy are not very high (RR=23-52%). Globally, both of these approaches remain very expensive on an industrial scale and not very productive.

The authors of the present invention have sought to develop a method for synthesizing 2HBL which does not have these drawbacks while remaining a simple, inexpensive and efficient method.

HMTBA is an analog of methionine, an essential amino acid, and finds considerably extensive applications notably in humans as a food supplement or drug, as well as in animal nutrition, as a bio-available source of methionine. The derivatives of this analog, notably its esters and its salts are also used in the same indications, some of them, such as HMBA isopropyl ester, having properties superior to those of HMBA. The HMBA is produced on an industrial scale according to perfectly well-established methods, in an amount of several hundred thousand metric tons/year. Its use as a synthesis substrate thus opens up an additional future for it.

It is in this context that the authors of the present invention have elaborated a method for synthesizing 2HBL from HMTBA and its derivatives, which, as compared with the aforementioned synthesis methods, may be applied in industrial amounts. The developed method is conducted in at most three steps, the reaction conditions of which are flexible and which are characterized by high transformation rates.

It further has the advantages of leading to a 2HBL which may be easily isolated and purified and which does not produce salts in excess.

This method is therefore a real solution for the industrial synthesis of 2HBL, by raising the whole of the obstacles to which are confronted the aforementioned known methods.

Thus, a first object of the invention is a method for preparing 2HBL from a compound, or from its salt or from its oligomers, said compound fitting the formula (I)

wherein

R1 represents H

R2 represents a group selected from OH; OR4 and OCOR4 wherein R4 represents a group selected from linear, cyclic, alicyclic or branched alkyl groups having from 1 to 10 carbon atoms, and aryl groups having from 6 to 10 carbon atoms, optionally substituted with substituent(s) selected from linear or branched alkyl groups having from 1 to 10 carbon atoms, halogens and hydroxyl, amino, nitro and alkoxy groups having from 1 to 10 carbon atoms; and OSiRR'R" wherein R, R' and R" are selected independently of each other from linear, cyclic, alicyclic or branched alkyl groups having from 1 to 10 carbon atoms, aryl groups having from 6 to 10 carbon atoms, optionally substituted with substituent(s) selected from linear or branched alkyl groups having from 1 to 10 carbon atoms or R1 and R2 represent together =O, R3 represents COOH or a COOR5 group wherein R5 represents a group selected from linear, cyclic, alicyclic or branched alkyl groups having from 1 to 10 carbon atoms, benzyl groups substituted with one or two substituents selected from linear or branched alkyl groups having from 1 to 10 carbon atoms, halogens, and hydroxyl, amino, nitro and alkoxy groups having from 1 to 10 carbon atoms, or R3 represents a cyano group, a method according to which a sulfonium of said compound is obtained, said sulfonium fitting the formula (II)

wherein R1, R2 and R3 have the above definition, and R6 and R7 are selected independently of each other from H, linear, cyclic, alicyclic or branched alkyl groups having from 1 to 10 carbon atoms, and aryl groups having from 6 to 10 carbon atoms, optionally substituted with substituent(s) selected from linear or branched alkyl groups having from 1 to 6 carbon atoms, halides and hydroxyl, amino, nitro and alkoxy groups having from 1 to 10 carbon atoms; R8 is selected from H, linear, cyclic, alicyclic or branched alkyl groups having from 1 to 10 carbon atoms, aryl groups having from 6 to 10 carbon atoms, optionally substituted with substituent(s) selected from linear or branched alkyl groups having from 1 to 10 carbon atoms, and attractor groups notably those comprising a function selected from acid, ester, cyano functions, and X represents a counter-ion, and the thereby obtained sulfonium is hydrolyzed, and 2,4-dihydroxybutyric acid or its salt is cyclized into 2-hydroxybutyrolactone.

Before describing the invention in more details, the definition of terms used in this description and the claims is provided hereafter.

Definitions

By salt of a compound of formula I, is meant any compound of formula I wherein the hydrogen of the carboxylic group is replaced with a metal, notably an alkaline metal, an earth alkaline metal or a transition metal. This metal is preferentially selected from Na, Ca, Mn, Mg, Cr. It may be simple or multiple. Thus a calcium salt of 2-hydroxy-4-méthylthiobutanoic acid may be selected from the salts of formula $(HMTBA)_n$ Ca wherein n varies from 2 to 10. This notion of salt of course covers all mixtures of salts entering the above definition.

By oligomer of a compound of formula I, is meant any oligomer and notably dimer as it may coexist, including in trace amounts, with said compound when the latter is not used in the totally purified state.

By preparation of 2-hydroxybutyrolactone (2HBL), the intention is to cover all forms of 2HBL, either alone or as mixtures, notably its stereoisomers and its tautomers.

Depending on the sought forms, one skilled in the art will select the corresponding form(s) of the initial acid.

Within the scope of the present invention:

- An alkyl group designates a linear, cyclic, alicyclic or branched saturated hydrocarbon monovalent radical. As indicated, it has 1 to 10 carbon atoms, preferably 1 to 6 carbon atoms. As examples, the methyl, ethyl, n-propyl, isopropyl, n-butyl, isobutyl, tert-butyl, sec-butyl, pentyl, neopentyl, n-hexyl, cyclohexyl groups . . . enter this definition;
- An aryl group designates an aromatic hydrocarbon monovalent radical. As examples the phenyl, benzyl, tolyl, naphthyl, biphenyl groups enter this definition.
- An alkoxy group designates an O-alkyl radical, wherein the alkyl term meets the above definition;
- A counter-ion X is an entity which will ensure electric neutrality of the sulfonium of formula (II).

This method comprises the steps for obtaining the sulfonium, for hydrolyzing the sulfonium into 24DHBA, and for cyclizing the 24DHBA into 2HBL. As this will be indicated below, these steps are consecutive or concomitant depending on the reagents used.

The first step consists of obtaining an activated form of said compound or of its salt, the authors have unexpectedly discovered that the sulfonium form may lead to the formation of 2HBL as indicated above, notably under the conditions which will be described later on.

Documents FR2150605A1 and DE2161991A1 describe the preparation of the sulfonium from a 2-hydroxy-4-alkylthiobutyric acid and notably from HMTBA, by action of an alkyl halide, preferably in excess, on said acid, in the presence of water, at a temperature comprised between 10 and 100° C., and then by isolation of the sulfonium by extraction with an alcohol, after removing the water. According to the invention, the sulfonium may be obtained in this way or by any other suitable so-called alkylation reaction on the compound (I) or its salt.

For this first step, the reagent is preferably an agent of formula [CR6R7R8]X where R6, R7 and R8 are as defined above and X is selected from halogens and OH, sulfate, sulfonate and phosphate groups. When X designates a halogen, a preferred agent for applying a method of the invention at an industrial scale is selected from methyl iodide, bromo-acetic acid and benzyl bromide. When X designates OH, the agent is selected from alcohols having from linear or branched alcohols having from 2 to 6 carbon atoms and is preferably used in an acid medium, for example in the presence of sulfuric acid; an advantageous agent notably with respect to an industrial process, is tertio-butanol. In the case when the agent is an alcohol and notably tertio-butanol, a favorable reaction medium is an acid hydro-alcoholic medium.

According to another alternative, the sulfonium is obtained by reaction on the compound, of an agent of formula $[CR6R7R8]^+X^-$ wherein $[CR6R7R8]^+$ is a carbocation formed from a corresponding linear or branched alkene having from 2 to carbon atoms, in the presence of an acid. This acid will be selected by one skilled in the art from his/her general knowledge for forming the carbocation. This is preferably a mineral acid, for example sulfuric acid or hydrochloric acid.

Preferentially, the agent is of formula $[C(CH_3)_2H]^+X^-$ wherein X represents $HSO_4$ or Cl and is formed from propene in the presence of sulfuric acid or hydrochloric acid, respectively. According to another advantageous alternative, the agent is of formula $[C(CH_3)_3]^+X^-$ wherein X represents $HSO_4$ or Cl and is formed from isobutene in the presence of sulfuric acid or hydrochloric acid, respectively.

All the other agents leading to the formation of the sulfonium may of course be used. Moreover, the alkylation agent may be supported.

The step for hydrolyzing the sulfonium according to the method of the invention may be contemplated under all suitable conditions. As an example, it is carried out by simply heating the reaction medium directly from the previous alkylation step. Preferably the pH is not too high, advantageously it is maintained at a value of the order of 6.

The last step of the method of the invention is the cyclization of 24DHB into 2HBL which may be achieved by one skilled in the art under conditions for example described in the aforementioned documents AU2004200948A and WO2008/022953A1.

At least two, or even all the steps for forming the sulfonium, for hydrolyzing the sulfonium into 24DHBA and for cyclizing the 24DHBA may be simultaneous. Conditions for heating to a temperature varying from 30 to 150° C., preferentially from 60 to 100° C. are sufficient. The authors further observe that by adding halide salts, such as NaBr, it is possible to increase the reactivity and selectivity of these reactions.

As indicated earlier, the thereby formed 2HBL may be easily purified and isolated from the reaction medium. The examples which follow, will illustrate this but one skilled in the art will resort to his/her general knowledge in this field for proceeding therewith. Thus, all the well-known techniques by decantation, distillation . . . may be applied.

The present invention and its advantages are illustrated in the following examples.

In the experimental part hereafter, TT means transformation rate, RR yield on reagent, SAAT88 means AT88 acetic sulfonium, SBAT88, AT88 benzyl sulfonium, MHACa calcium salt of AT88, SBMHACa, MHACa benzyl sulfonium, $T_{DE}$ and $T_{MR}$ temperature of the jacket and of the reaction medium respectively, DCM, dichloromethane.

EXAMPLE 1

Preparation of 2HBL from HMTBA (or AT88) Via a Sulfonium Obtained by Reaction of Bromoacetic Acid 1.1. Preparation of 24DHBA:

Reaction Scheme:

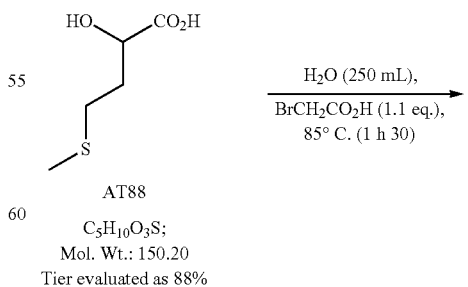

AT88

$C_5H_{10}O_3S$;
Mol. Wt.: 150.20
Tier evaluated as 88%

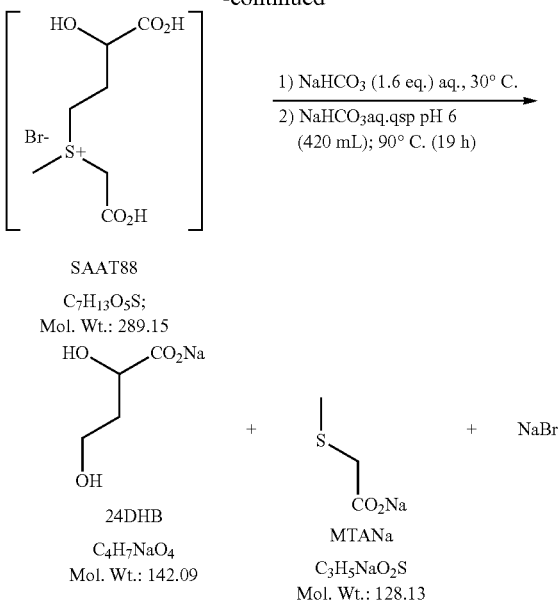

Reagents and Table of the Loads:

| Reagents | Molecular weight | Quality % | Density (g/ml) | Amount (g) | Volume (ml) | mmol | Eq. |
|---|---|---|---|---|---|---|---|
| AT88 | 150.2 | 88 | — | 50.0 | — | 293 | 1.0 |
| BrCH$_2$CO$_2$H | 138.9 | >98% | — | 45.4 | — | 326 | 1.1 |
| Water | — | deionized | 1.0 | 250 | 250 | — | — |
| NaHCO$_3$ | 84.0 | — | — | 39.1 | — | 466 | 1.6 |
| NaHCO$_3$aq. | 84.0 | 8.7% | — | (36.5) | 420 | 435 | 1.5 |

Operating Conditions and Results:

1.1.1. Alkylation

In a 500 mL jacketed reactor equipped with a condenser, a thermometer and mechanical stirring with four tilted blades, are successively introduced at 20° C.: 50 g of HMTBA and 200 mL of deionized water ($T_{DE}$=20° C.). The medium is stirred at 400 rpm (milky solution) and then bromoacetic acid (45.4 g, 1.1 eq., no exothermy) is added within 5 minutes and rinsing is performed with 50 mL of deionized water. 8 minutes after addition of BrCH$_2$CO$_2$H, an orangey limpid medium (stirring at 400 rpm) is obtained, no clear exothermy ($T_{MR}$=20° C., $T_{DE}$=20° C. 10 minutes after adding the bromoacetic acid).

Heating of the medium with stirring (400 rpm) up to 80-85° C. (set value $T_{MR}$=80° C. reached within 30 minutes, $T_{DE}$=95° C.).

Maintaining heating and stirring for 1 h 30 mins at 80-85° C. ($T_{DE}$=80° C. (30 min) and then $T_{DE}$=85° C. (1 h)). An orangey limpid liquid is obtained.

Sampling for $^1$H NMR analysis (100 μL of crude solution +500 μL D$_2$O).

Stopping Criterion: residual AT88<1% mol (triplet δ=2.4 ppm, 2H, D$_2$O)⇒ compliant result.

1.1.2. Hydrolysis at pH 6

The previous crude reaction mixture is cooled down to 30° C. with stirring (300 rpm, set value $T_{MR}$=30° C. reached within 20 minutes, $T_{DE}$=20° C.). A pH probe is introduced into the same reactor. Once the medium is at 30° C., solid NaHCO$_3$ (39 g, 1.6 eq.) is added portionwise within 30 minutes; strong <<delayed>> effervescence. At the end of the addition, measured pH=3.1 at 25° C. Orangey limpid solution.

Heating the medium to 90° C. (set value $T_{MR}$=90° C. reached within 30 minutes, $T_{DE}$=95° C.). Stirring at 400 rpm.

At $T_{MR}$=90° C. (30 minutes after starting the heating; measured pH=3.0), the regulation of the pH is started with the set value pH=6 by adding an 8.7% NAHCO$_3$ aqueous solution (via a syringe pump controlled by a computer).

After 3 h 30 mins of regulation, the amount of added NaHCO$_3$ is 410 mL (pH=6.0). The stirring is reduced to 100 rpm and the heating is maintained for the whole night ($T_{DE}$=95° C., $T_{MR}$=90° C.).

After 19 h of regulation, the pH of the medium is 6.1. Sampling of the aqueous phase (100 μL+500 μL D$_2$O) for $^1$H NMR analysis.

Stopping Criterion: disappearance of the characteristic signal of SAAT88 (singlet δ=2.81 ppm and multiplet at δ=3.33 ppm, D$_2$O)⇒ compliant result (SAAT88 non detected.)

Return to 25° C. within 1 h 30 mins with mild stirring.

748 g of aqueous crude is obtained.

Results:

TT$_{AT88}$>99% (step 1, estimated by $^1$H NMR)

RR$_{24DHB}$=95% (assayed by $^1$H NMR)

RR$_{MTANa}$=95% (assayed by $^1$H NMR)

Residual AT88: <2 mol % (estimated by $^1$H NMR)

1.2 Synthesis and isolation of 2HBL from 24DHB

Reaction Scheme:

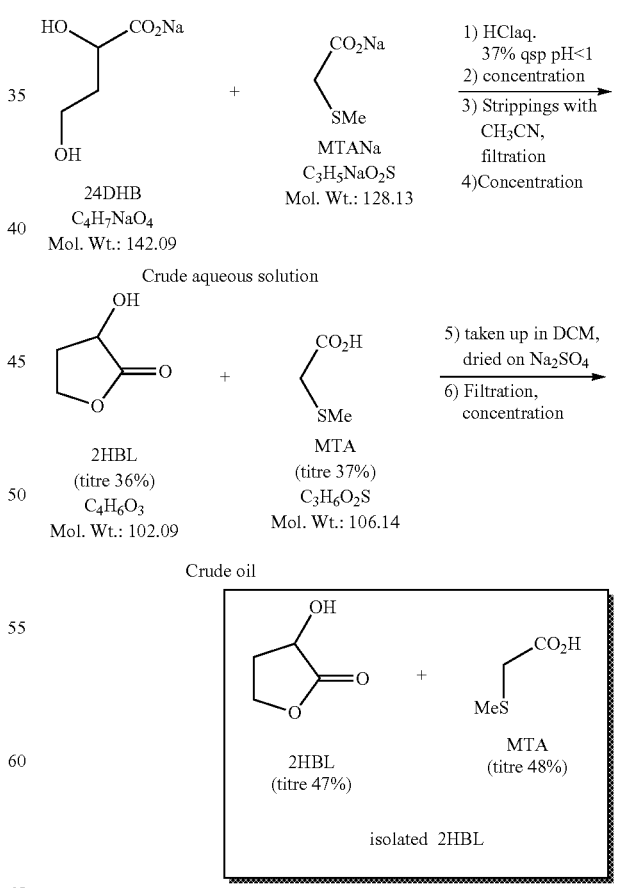

Reagents and Table of the Loads:

| Reagents | Molecular Weight | Quality % | Density (g/mL) | Amount (g) | Volume (mL) | mmol | Eq. |
|---|---|---|---|---|---|---|---|
| Aqueous crude | 142.1 | 0.37 mmol/g | — | 74.8 | — | 27.8 | 1.0 |
| 37% HCl$_{aq}$. | 36.5 | 37% | 1.2 | 7.2 | 6 | 73 | qsp pH < 1 |
| Acidified aqueous crude | 120.1 | 0.34 mmol/g | — | 82 | — | 27.8 | 1.0 |
| CH$_3$CN | — | HPLC | — | — | 2 × 100 + 100 | — | — |
| Crude oil | 102.1 | — | — | 1.0 | — | — | — |
| DCM | — | PA | 1.33 | — | 40 | — | — |
| Na$_2$SO$_4$ | — | Anhydrous | — | 2.0 | — | — | — |

Operating Conditions and Results:

a) Acidification

In a 250 mL 3-neck flask provided with magnetic stirring and equipped with a pH electrode, are introduced the 74.8 g of the aqueous solution of 24DHB and then 37% HCl$_{aq}$. Is added dropwise down to pH=0.5 (addition of 6 mL). Limpid orangey solution.

b) Concentration and strippings with CH$_3$CN

The previously prepared acidified solution is introduced into a 250 mL flask and concentrated under reduced pressure (20 mbars, 60° C.). The crude concentrate (oil+solid) is taken up with 100 mL of acetonitrile, and the obtained suspension is then concentrated (60° C., 20 mbars). This operation is renewed once and 100 mL of acetonitrile are then added and the obtained suspension is filtered on a frit of porosity No. 3; the salts and insolubles are rinsed with 2×10 mL of acetonitrile and the filtrate is then concentrated (17 mbars, 60° C.). 6.6 g of a pale yellow-orangey oil are obtained.

c) Drying on Na$_2$SO$_4$

In a 100 mL Schott tube provided with magnetic stirring, 1.0 g of crude oil obtained earlier are dissolved by 40 mL of dichloromethane (cloudy, milky solution and slight presence of a gum residue) and then 2 g of Na$_2$SO$_4$ are added with stirring. The stirring is maintained for 30 minutes followed by filtration on a frit of porosity No. 3 (limpid filtrate); rinsing of the salts with 40 mL of DCM. The filtrate is concentrated under reduced pressure (19 mbars, 35° C.).

0.75 g of a pale yellow oil are obtained. $^1$H NMR analysis (CDCl$_3$)

Results (Assayed by $^1$H NMR):

RR$_{2HBL}$=82%; titer 2HBL=47% (from 24DHB)
RR$_{MTA}$=81%; titer MTA=48% (from MTANa)

EXAMPLE 2

Preparation of 2HBL from HMTBA (or AT88) Via a Sulfonium Obtained by Reaction of Benzyl Bromide 2.1. Preparation of 24DHBA:
Reaction Scheme:

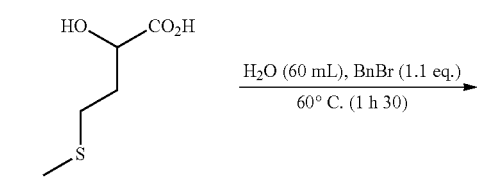

AT88
C$_5$H$_{10}$O$_3$S; Mol. Wt.: 150.20
Titre evaluated as 88%

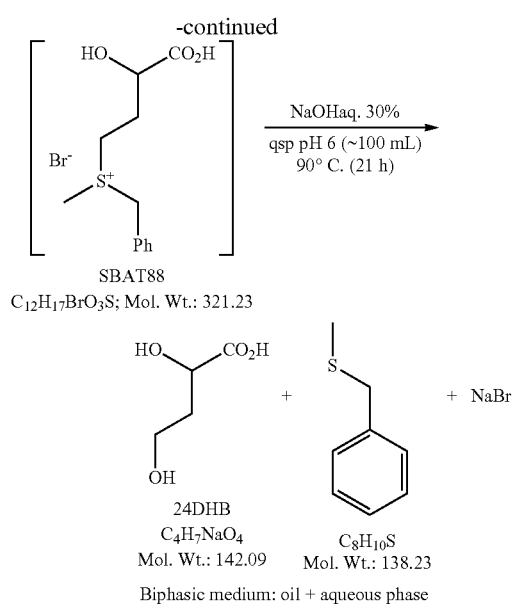

SBAT88
C$_{12}$H$_{17}$BrO$_3$S; Mol. Wt.: 321.23

24DHB
C$_4$H$_7$NaO$_4$
Mol. Wt.: 142.09

C$_8$H$_{10}$S
Mol. Wt.: 138.23

Biphasic medium: oil + aqueous phase

Reagents and Table of the Loads:

| Reagents | Molecular Weight | Quality % | Density (g/mL) | Amount (g) | Volume (mL) | mmol | Eq. |
|---|---|---|---|---|---|---|---|
| AT88 | 150.2 | 88 | — | 60 | — | 352 | 1.0 |
| BnBr | 171.0 | 100 | 1.438 | 66 | 46 | 383 | 1.09 |
| Water | — | Deionized | 1.0 | 60 | 60 | — | — |
| 30% NaOH$_{aq}$. | 40.0 | 7.5N | — | — | 100 | 750 | 2.13 |

Operating Conditions and Results:

1) Alkylation

In a 250 mL jacketed reactor equipped with a condenser, a thermometer and 4-blade mechanical stirring, are successively introduced at 25° C.: 60 g of AT88 and 60 mL of deionized water (T$_{DE}$=25° C.). The medium is stirred at 500 rpm (beige emulsion) and then benzyl bromide (46 mL, 1.1 éq.) is added within 3 minutes; biphasic medium, stirred at 1,000 rpm in order to obtain a well emulsified medium (pale brown milky medium). The addition of BNBr is exothermic (6 minutes after adding BnBR: T$_{MR}$=36° C., T$_{DE}$=25° C.).

Heating the medium with stirring (1,000 rpm) up to 62° C. (set value T$_{MR}$=62° C. reached within 30 minutes, T$_{DE}$=65° C.).

Maintaining the heating and the stirring for 1 h 30 mins and at 62° C. (T$_{DE}$=65° C.). An orangey limpid solution is obtained.

Sampling for ¹HNMR analysis (50 μL of crude solution +500 μL D₂O).

Stopping Criterion: disappearance of the characteristic signal of AT88 (triplet δ=2.4 ppm, D₂O)⇒ compliant result (AT88 not detected).

2) Hydrolysis at pH 6

A pH probe is introduced into the same reactor. Heating of the medium to 90° C. (set value $T_{MR}$=91° C. reached within 30 minutes, $T_{DE}$=100° C. and then 93° C.). Stirring at 700 rpm.

At $T_{MR}$=85° C. (24 minutes after starting the heating; measured pH=−0.6), sampling of the medium is carried out for ¹H NMR analysis (50 μL +500 μL D₂O) in order to check formation of AT88 before the beginning of the regulation⇒ confirmed presence of AT88 (characteristic signals: triplet δ=2.4 ppm and singlet δ=1.87 ppm).

Regulation of the pH is started after the sampling with the set value pH=6 by adding 30% soda (via a syringe pump controlled by a computer). At pH=3.5, the reaction medium becomes turbid and milky (3 minutes of regulation). After 7 minutes of regulation (pH=6.0, set value reached), formation of a floating orangey oil. After 1 h of regulation, significant presence of oily supernatant. Stirring at 400 rpm.

After 5 h of regulation, the added amount of soda almost no longer varies (pH=6.13). The stirring is reduced to 100 rpm and the heating is maintained for the whole of the night ($T_{DE}$=93° C., $T_{MR}$=90° C.).

After 19 h of regulation, the pH of the medium is 6.04. Sampling of the aqueous phase (50 μL+500 μL D₂O) and of the floating oil (30 mg+600 μL CDCl₃) for ¹H NMR analysis.

Stopping Criterion: disappearance of the characteristic signal of SBAT88 (singlet δ=2.58 ppm, D₂O)⇒ compliant result (SBAT88 not detected).

Return to 25° C. within 3 h with mild stirring. Both phases are separated by simple decantation and drawn off.

142 g of brown oil and 245 g of aqueous crude medium are obtained.

Results:

$TT_{AT88}$=100% (step 1, estimated by ¹H NMR)

$RR_{24DHB}$=83% (assayed by ¹H NMR)

$RR_{AT88}$=8% (assayed by ¹H NMR)

2.2. Synthesis and Isolation of 2HBL from 24DHB

Reaction Scheme:

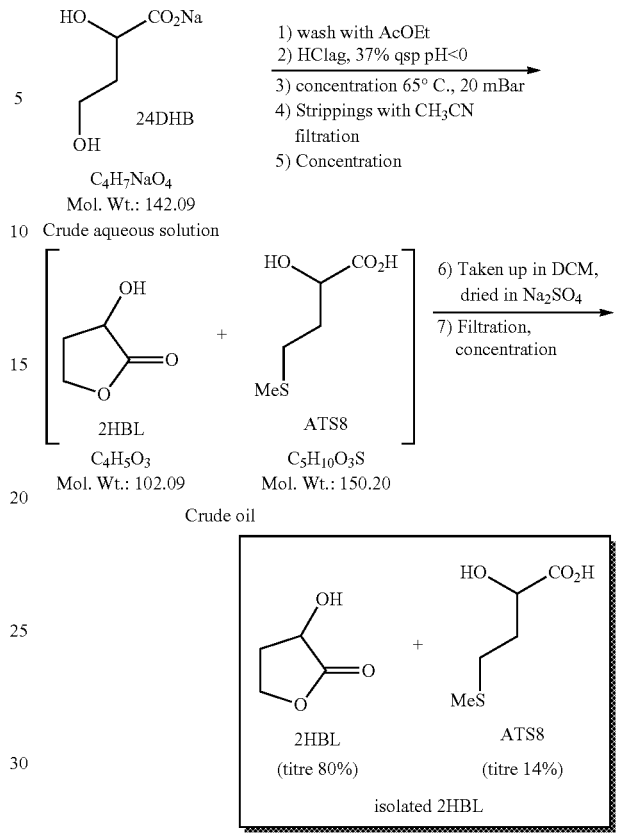

Reagents and Table of the Loads:

| Reagents | Molecular | | Density | Amount | Volume (mL) | mmol | Eq. |
|---|---|---|---|---|---|---|---|
| Aqueous crude medium | 142.1 | 1.2 mmol/g | — | 50 | — | 59.6 | 1.0 |
| AcOEt | — | PA | | — | 3 × 15 ml | — | — |
| HClaq. 37% | 36.5 | 37% | 1.2 | 7.2 | 6 | 73 | qsp pH |
| Acidified washed aqueous crude | 120.1 | 1.2 mol/g | — | 12.6 | — | 14.6 | 1.0 |
| CH₃CN | — | HPLC | | — | 3 × 50 + 50 | — | |
| Crude oil | 102.1 | — | — | 1.735 | — | — | — |
| DCM | — | PA | 1.33 | — | 50 | — | — |
| Na₂SO₄ | — | Anhydrous | — | 2.0 | — | — | — |

Operating Conditions and Results:

a) washings with AcOET

In a 100 ml Schott tube, are successively introduced 50 g of crude aqueous phase isolated by simple decantation of the reaction crude medium from hydrolysis and then 15 mL of ethyl acetate.

Intensive stirring and decantation. The organic phase is removed. Washing with AcOEt of the aqueous phase is reproduced twice.

49.1 g of aqueous crude medium, a limpid orangey solution are obtained. ¹H NMR analysis (100 μL+500 μL D₂O).

Stopping Criterion: benzyl residues <1 mol % evaluated by comparison of the characteristic benzyl signal (bulk, δ=7.3 ppm, D₂O) with that of 24DHB (characteristic signal δ=3.62 ppm)⇒ compliant result (benzyl residues <1 mol %).

b) Acidification

In a 100 mL 3-neck flask provided with magnetic stirring and equipped with a pH electrode, are introduced the 49 g of the previous aqueous solution and then 37% HClaq. Is added dropwise down to a pH=−0.5 (addition of 6 mL). Limpid orangey solution.

c) Concentration and CH$_3$CN Strippings.

12.3 g of the acidified solution are introduced into a 100 mL flask and concentrated under reduced pressure (20 mbars, 65° C.). The concentrated crude product (oil+solid) is taken up with 50 mL of acetonitrile, and the obtained suspension is then concentrated (65° C., 20 mbars). This operation is renewed three times and then 50 mL of acetonitrile are added and the obtained suspension is filtered on a frit of porosity No. 3, the salts and insolubles are rinsed with 2×5 mL of acetonitrile and the filtrate is then concentrated (20 mbars, 65° C.). 1.73 g of a pale yellow-orangey oil are obtained.

d) Drying on Na$_2$SO$_4$

In a 100 mL 3-neck flask provided with magnetic stirring, 1.73 g of the crude oil obtained previously are dissolved with 50 mL of dichloromethane (cloudy solution, slight formation of off-white flakes which decant) and then 2 g of Na$_2$SO$_4$ are added with stirring. The stirring is maintained for 30 minutes and followed by filtration on a frit of porosity No. 3 (slightly cloudy filtrate); rinsing of the salts with 2×25 mL of DCM. The filtrate is concentrated under reduced pressure (18 mbars, 35° C.).

1.52 g of pale yellow oil are obtained. $^1$H NMR analysis (CDCl$_3$)

Results (Assayed by $^1$H NMR):
RR$_{2HBL}$=81%; titer 2HBL=80%
RR$_{AT88}$=8%; titer AT88=14%

EXAMPLE 3

Preparation of 2HBL from a Calcium Salt of HMTBA Via a Sulfonium significant formation of 24DHB. Under the tested conditions, the presence of water is therefore required for displacement of the sulfonium.

EXAMPLE 4

"1 Pot" Preparation of 2HBL and Effect of Adding a Salt (NaBr)

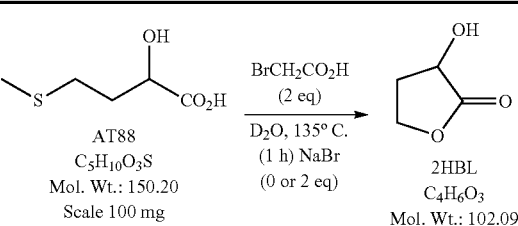

| Test | NaBr (number of eq.) | Results ($^1$HNMR) | | |
|---|---|---|---|---|
| | | TT$_{AT88}$ | TT$_{SAAT88}$ | 2HBL formation |
| A | 0 | 100 | <10 | Low |
| B | 2 | | >90 | Clearly detected |

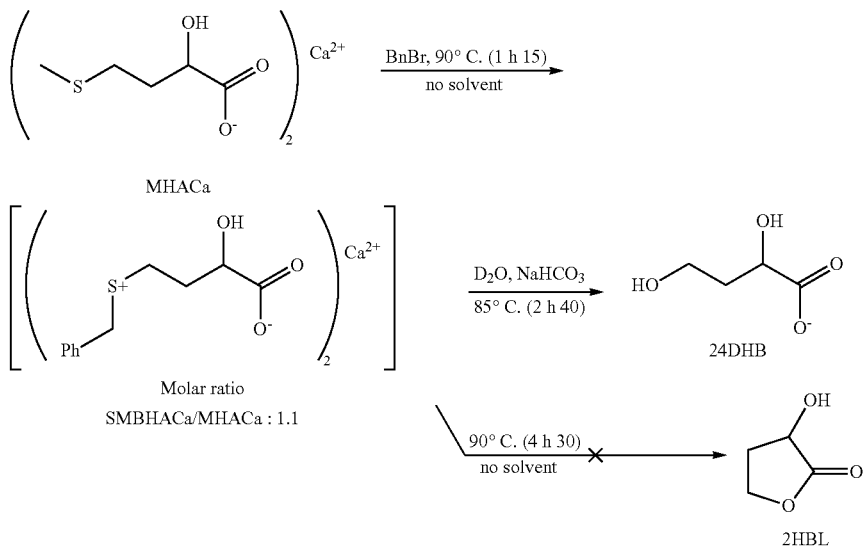

The formation of 2HBL (or of derived open forms) is not observed even after extended heating to 90° C. (4 h 30 min) of the alkylation crude product. Conversely, the effect of adding water and sodium hydrogen carbonate onto the alkylation crude product (qsp pH 8) followed by heating is expressed by The conditions used for test B were reproduced with the following performances ($^1$H NMR assay, after 3 hours at 135° C.): complete $TT_{SAAT88}$, $RR_{2HBL}$=33-39%.

EXAMPLE 5

Preparation of HMBA Methyl Sulfonium

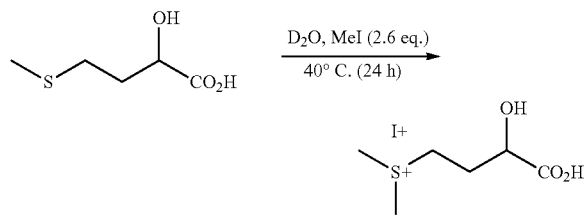

Operating conditions: 5 mL mini-reactor; at 25° C., introduction of AT88 (644 mg), D$_2$O (3 mL), MeI (478 μL) and then heating to 40° C. for 24 hours. Concentration of the totality of the reaction medium (18 mbars, 65° C.).
Results (assayed by $^1$H NMR): TT AT88>95%, RRisolated (sulfonium)=89%, titer (sulfonium)=70%

EXAMPLE 6

Preparation of HMBA Tert-Butyl Sulfonium

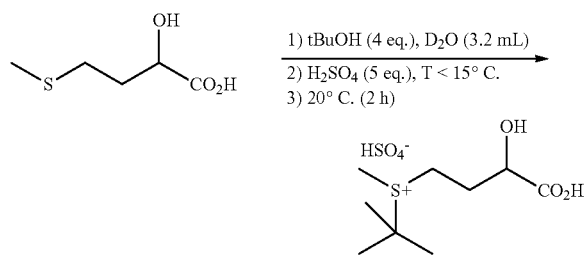

Operating conditions: 30 mL Schott tube; at 25° C., introduction of AT88 (3.4 g), D$_2$O (3.2 mL), tBuOH (7.64 mL) and then cooling down to 10° C. and adding H$_2$SO$_4$ (5.2 mL, 5 eq.) for 20 minutes by maintaining a temperature T<15° C.; returned to 20° C. after the end of the addition of acid and 20° C. is maintained for 2 h.
Results (estimated by $^1$H NMR): complete TT AT88, RRassayed (sulfonium)>90%

The invention claimed is:

1. A method for preparing 2-hydroxybutyrolactone (2HBL) from a compound, or from its salt or its oligomers, said compound fitting formula (I)

CH3-S—CH2CH2CR1R2R3 wherein

R1 represents H
R2 represents OH; or
R1 and R2 together represent =O;
R3 represents COOH or COO—CH(CH$_3$)$_2$,
method according to which
a sulfonium of said compound is obtained, said sulfonium fitting the formula (II)

[CH3][CH2CH2CR1R2CR3][CR6R7R8]S+X- wherein R1, R2 and R3 have the above definition, and R6 and R7 are selected independently of each other from H and linear, cyclic, alicyclic or branched alkyl groups having from 1 to 10 carbon atoms; R8 is selected from H, CH3, phenyl, COOH, and linear, cyclic, alicyclic or branched alkyl groups having from 1 to 10 carbon atoms, and
the thereby obtained sulfonium is hydrolyzed, and
2,4-dihydroxybutyric acid or its salt is cyclized into 2 hydroxybutyrolactone.

2. The method according to claim 1, wherein the compound of formula (I) is selected from 2-hydroxy-4-methylthiobutyric acid (HMTB), 2-oxo-4-methylthiobutyric acid (KMB), HMTB isopropyl ester (HMBI), salts thereof and oligomers thereof.

3. The method according to claim 1, wherein the sulfonium is obtained by reaction on the compound, of an agent selected from agents of formula [CR6R7R8]X wherein X is selected from halogens and OH, sulfate, sulfonate and phosphate groups.

4. The method according to claim 3, wherein said agent is selected from bromoacetic acid and benzyl bromide.

5. The method according to claim 4, wherein agent is selected from linear or branched alcohols, having from 2 to 6 carbon atoms and is used in an acid medium.

6. The method according to claim 3, wherein the sulfonium is obtained by reaction on the compound of an agent of formula [CR6R7R8]+X-wherein [CR6R7R8]+is a carbocation formed from a corresponding linear or branched alkene having from 2 to 10 carbon atoms, in the presence of an acid.

7. The method according to claim 6, wherein the agent is of Currently amended [C(CH3)2H]+X- wherein X represents HSO4 or Cl and is formed from propene in the presence of sulfuric acid or hydrochloric acid respectively.

8. The method according to claim 6, wherein the agent is of formula [C(CH3)3]+X- wherein X represents HSO4 or Cl and is formed from isobutene in the presence of sulfuric acid or hydrochloric acid respectively.

9. The method according to claim 1, wherein at least two of the reactions for forming the sulfonium, for hydrolyzing the sulfonium and for cyclizing 2,4-dihydroxybutyric acid (24DHBA) are simultaneous.

10. The method according to claim 9, wherein the reaction temperature varies from 30 to 150° C.

11. The method according to claim 9, wherein halide salts such as NaBr are added.

12. The method according to claim 1, wherein it is applied on an industrial scale.

13. The method of claim 11 wherein the halide salt is NaBr.

* * * * *